US012349976B2

(12) United States Patent
Kim et al.

(10) Patent No.: US 12,349,976 B2
(45) Date of Patent: Jul. 8, 2025

(54) NON-CONTACT PORTABLE TONOMETRY SYSTEM AND TONOMETRY METHOD USING DIFFERENCE IN INFRARED INTENSITY

(71) Applicants: KNU-INDUSTRY COOPERATION FOUNDATION, Chuncheon-si (KR); C&V TECH INC., Wonju-si (KR)

(72) Inventors: Byeong Hee Kim, Chuncheon-si (KR); Young Ho Seo, Chuncheon-si (KR); Hyung Jin Kim, Chuncheon-si (KR); Min Jae Jeong, Chuncheon-si (KR); Dong Uk Kim, Samcheok-si (KR); Jin Hue Kang, Seoul (KR)

(73) Assignees: KNU-INDUSTRY COOPERATION FOUNDATION, Chuncheon-si (KR); C&V TECH INC., Wonju-si (KR)

( * ) Notice: Subject to any disclaimer, the term of this patent is extended or adjusted under 35 U.S.C. 154(b) by 831 days.

(21) Appl. No.: 17/607,751

(22) PCT Filed: Jul. 30, 2020

(86) PCT No.: PCT/KR2020/010031
§ 371 (c)(1),
(2) Date: Oct. 29, 2021

(87) PCT Pub. No.: WO2021/025368
PCT Pub. Date: Feb. 11, 2021

(65) Prior Publication Data
US 2022/0218203 A1    Jul. 14, 2022

(30) Foreign Application Priority Data

Aug. 8, 2019  (KR) .................... 10-2019-0096748

(51) Int. Cl.
*A61B 3/16* (2006.01)
*G01J 1/08* (2006.01)

(52) U.S. Cl.
CPC ................ *A61B 3/165* (2013.01); *G01J 1/08* (2013.01)

(58) Field of Classification Search
CPC ........... A61B 3/165; A61B 3/152; A61B 5/00; A61B 3/00; A61B 3/16; A61B 5/0059; G01J 1/08
See application file for complete search history.

(56) References Cited

U.S. PATENT DOCUMENTS

| 5,031,623 A | 7/1991 | Kohayakawa et al. |
| 2001/0009973 A1* | 7/2001 | Miwa ..................... A61B 3/165 600/399 |
| 2004/0189936 A1* | 9/2004 | Mimura ................. A61B 3/165 351/205 |

FOREIGN PATENT DOCUMENTS

| JP | 63-097141 A | 4/1988 |
| JP | 02-167134 A | 6/1990 |

(Continued)

*Primary Examiner* — Tse W Chen
*Assistant Examiner* — Joseph A Tombers
(74) *Attorney, Agent, or Firm* — NKL Law; Jae Youn Kim

(57) ABSTRACT

The present invention relates to a non-contact portable tonometry system and tonometry method using a difference in infrared intensity. A nozzle module receives compressed air from a compressed air supply source and sprays the same through an air spray port to a cornea of a subject, thus to cause corneal deformation. An infrared ray sensor is disposed in the nozzle module to emit infrared rays to the cornea and measure an amount of light reflected from the cornea. A controller converts the amount of light measured by the infrared ray sensor before and after the deformation of corneal into intraocular pressure.

2 Claims, 4 Drawing Sheets

(56) References Cited

FOREIGN PATENT DOCUMENTS

KR        10-1093217 B1   12/2011
KR   10-2019-0074637 A   6/2019

\* cited by examiner

NON-CONTACT PORTABLE TONOMETRY SYSTEM AND TONOMETRY METHOD USING DIFFERENCE IN INFRARED INTENSITY

TECHNICAL FIELD

The present invention relates to a tonometry system for measuring intraocular pressure, which allows a user to early diagnose and prevent glaucoma and the like.

BACKGROUND ART

Glaucoma is one of the three major eye diseases that cause blindness along with diabetic retinopathy and macular degeneration. Because there is no specific symptom from the beginning to the end of the onset of disease, when a patient receives a diagnosis of having glaucoma, there are many cases of receiving a diagnosis as end-stage glaucoma in which the disease has been already progressed.

The major cause of glaucoma is that when a liquid, called the aqueous humor, filling a space between the cornea and the iris is generated more than in normal people, or when the flow of aqueous humor is hindered to cause a reduction in discharge, the intraocular pressure is increased. The increased intraocular pressure presses on the optic nerve present in the retina or causes damage, and eventually leads to blindness. Therefore, in order to diagnose and prevent glaucoma at an early stage, there is a need for a system for measuring intraocular pressure (also referred to as a 'tonometry system') that enables patients to periodically measure and manage intraocular pressure by themselves.

The conventional tonometry system may be classified into contact type and non-contact type tonometry systems. The contact-type tonometry system may be again classified into intraocular pressure type and applanation type tonometers, wherein the former uses a method in which a plunger is directly brought into contact with the cornea, then a displacement of the plunger is measured, and the measured displacement is converted into intraocular pressure, and the latter uses a method in which a pressure body is brought into contact with the eyeball, then a force to flatten a certain area of the cornea is measured, and the measured force is converted into intraocular pressure.

The biggest problem of the contact-type tonometry system is that it requires eye drop anesthesia by an expert, and corneal damage and infection of infectious eye disease occur as the plunger or the pressure body directly comes into contact with the cornea. On the other hand, the non-contact tonometry system has advantages of short measurement time and no need for eye drop anesthesia, whereas has disadvantages in that, when the corneal surface is irregular, the obtained measurement value is inaccurate, such that there is a limitation in miniaturization, and it is expensive.

SUMMARY OF INVENTION

Problems to be Solved by Invention

An object of the present invention is to provide a non-contact portable tonometry system and method for measuring intraocular pressure using a difference in infrared intensity, which enable a user to perform periodic eye examination and early detection of glaucoma by diagnosing glaucoma in advanced stages at home, thus to minimize damage due to the disease.

Means for Solving Problems

In order to achieve the above object, according to an aspect of the present invention, there is provided a non-contact portable tonometry system for measuring intraocular pressure using a difference in infrared intensity, which includes: a nozzle module; an infrared ray sensor; and a controller. The nozzle module is configured to receive compressed air from a compressed air supply source and spray it into a cornea of a subject through an air spray port, thus to cause a corneal deformation. The infrared ray sensor is disposed in the nozzle module to emit infrared rays to the cornea and measure an amount of light reflected from the cornea. The controller is configured to convert the amount of light measured by the infrared ray sensor before and after the deformation of the cornea into intraocular pressure.

Herein, the infrared ray sensor may include a sensor support block disposed in the nozzle module, a light emitting element supported by the sensor support block to emit infrared rays to the cornea, a pair of light receiving elements respectively disposed on both sides of the light emitting element and supported by the sensor support block to receive the light reflected from the cornea and measure the amount of light.

In addition, the nozzle module may include a nozzle body in which the sensor support block is fixed at a central portion thereof and an air supply port for receiving the compressed air from the compressed air supply source is formed at an outer circumference portion thereof, and a nozzle tip which has the air spray port formed in a central portion thereof to accommodate the sensor support block together with the nozzle body, and is configured to receive the compressed air supplied through the air supply port between the nozzle body and the nozzle tip to spray it through the air spray port.

According to a further embodiment, the non-contact portable tonometry system using a difference in infrared intensity may include a pressure sensor disposed in the nozzle module to receive the compressed air which is sprayed from the nozzle module and reflected by the cornea to measure pneumatic pressure. Herein, the controller converts the pneumatic pressure measured by the pressure sensor before and after the deformation of the cornea into intraocular pressure in connection with the amount of light measured by the infrared ray sensor.

According to another aspect of the present invention, there is provided a method for measuring intraocular pressure using a difference in infrared intensity, which includes: spraying compressed air into a cornea of a subject through an air spray port, thus to cause a corneal deformation, emitting infrared rays to the cornea to measure an amount of light reflected to the air spray port from the cornea by an infrared ray sensor, and converting the amount of light measured by the infrared ray sensor before and after the deformation of the cornea into intraocular pressure.

Herein, the step of measuring the amount of light may include emitting infrared rays to the cornea by a light emitting element, and receiving the light reflected from the cornea by the light receiving elements disposed on both sides of the light emitting element to measure the amount of light.

According to a further embodiment, the method may include: after the step of spraying compressed air to cause a corneal deformation, receiving the compressed air reflected from the cornea to measure pneumatic pressure by a pressure sensor, and in this case, the pneumatic pressure measured by the pressure sensor before and after the deformation of the cornea may be converted into intraocular pressure in connection with the amount of light measured by the infrared ray sensor.

Advantageous Effects

According to the present invention, the non-contact tonometry allows the subject to use it hygienically without any objection, and the infrared ray sensor is integrated into the nozzle module to make the system compact and portable. In addition, even if the corneal surface is irregular, it is possible to accurately measure the intraocular pressure, and by applying a relatively inexpensive infrared ray sensor, the system can be easily developed for home use. As a result, even at home, patients can diagnose glaucoma in advance by themselves, enabling periodic eye examinations and early detection of glaucoma, and thereby minimizing damage due to the disease.

MODE FOR CARRYING OUT INVENTION

Figure 1:
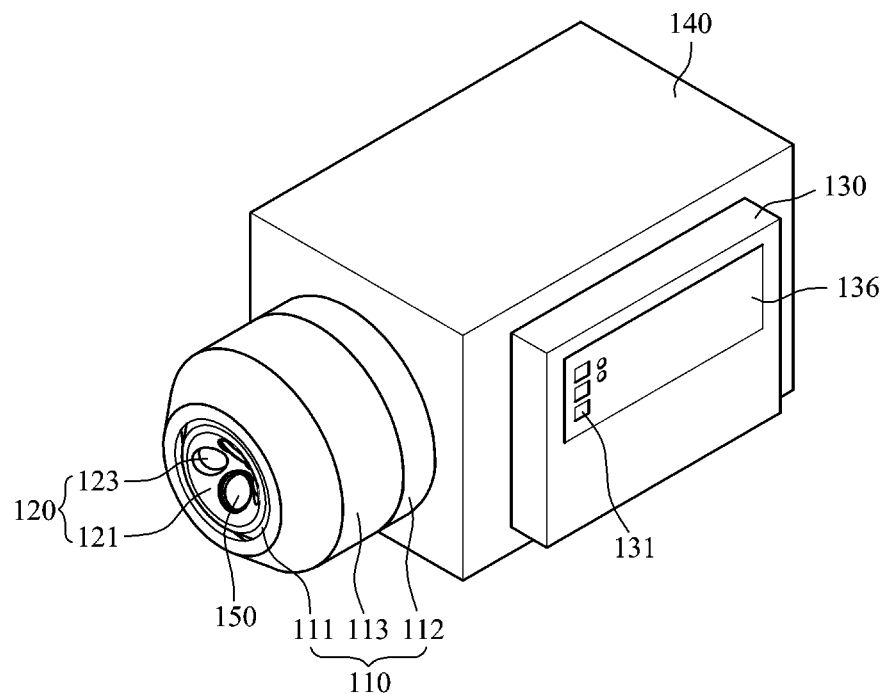
FIG. 1 is a perspective view illustrating a non-contact portable tonometry system using a difference in infrared intensity according to an embodiment of the present invention.

Hereinafter, the present invention will be described in detail with reference to the accompanying drawings. Herein, same reference numerals will be denoted to the same configuration, and repeated descriptions as well as the publicly known functions and configurations that are judged to be able to make the purport of the present invention unnecessarily obscure will not be described in detail. Such examples are provided for completely describing explaining the present invention to persons having ordinary knowledge and skills in the related art. Therefore, shapes and sizes of elements in the drawings may be exaggerated for clearer description.

Figure 2:
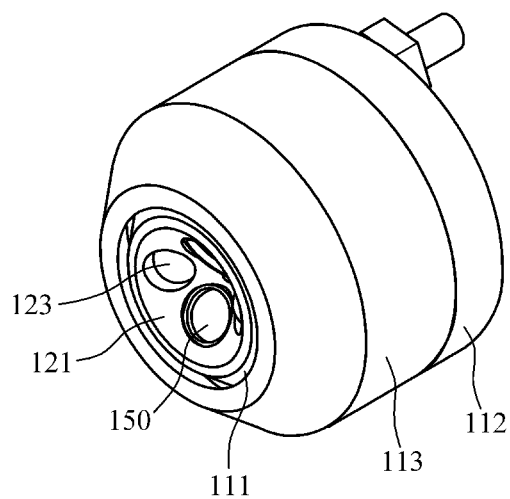
FIG. 2 is a perspective view illustrating a nozzle module extracted from the system shown in FIG. 1.
Figure 3:
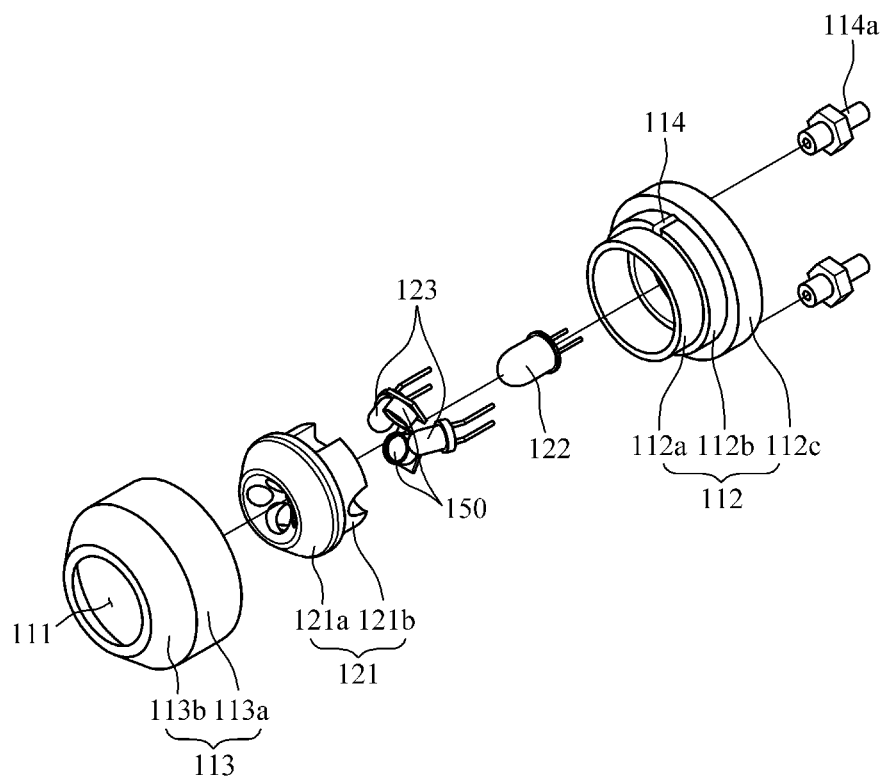
FIG. 3 is an exploded perspective view of the nozzle module shown in FIG. 2.
Figure 4:
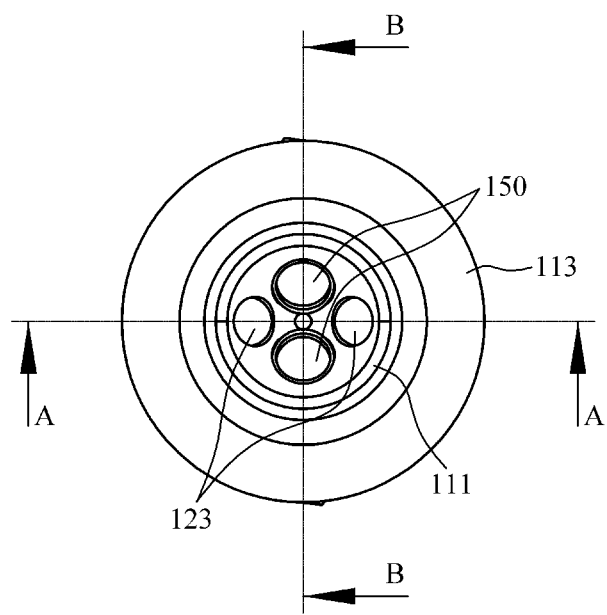
FIG. 4 is a front view of the nozzle module shown in FIG. 2.
Figure 5:
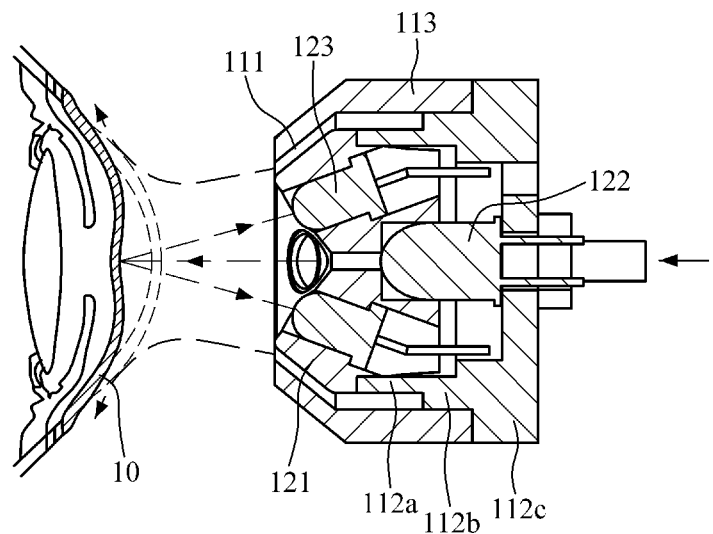
FIG. 5 is a cross-sectional view taken on line A-A in FIG. 4.
Figure 6:
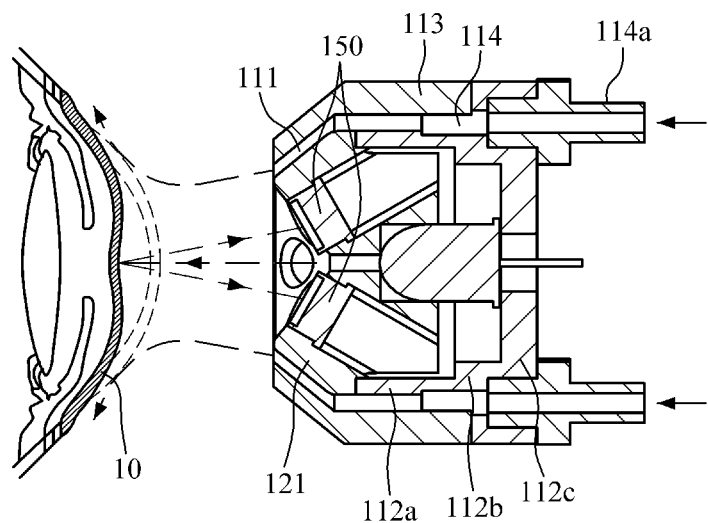
FIG. 6 is a cross-sectional view taken on line B-B in FIG. 4.

FIG. 1 is a perspective view illustrating a non-contact portable tonometry system using a difference in infrared intensity according to an embodiment of the present invention. FIG. 2 is a perspective view illustrating a nozzle module extracted from the system shown in FIG. 1. FIG. 3 is an exploded perspective view of the nozzle module shown in FIG. 2. FIG. 4 is a front view of the nozzle module shown in FIG. 2. FIG. 5 is a cross-sectional view taken on line A-A in FIG. 4. FIG. 6 is a cross-sectional view taken on line B-B in FIG. 4.

Referring to FIGS. 1 to 6, a non-contact portable tonometry system 100 using a difference in infrared intensity according to an embodiment of the present invention includes a nozzle module 110, an infrared ray sensor 120, and a controller 130.

The nozzle module 110 receives compressed air from the compressed air supply source 140 and sprays it into a cornea 10 of a subject through an air spray port 111, thus to cause a deformation in the cornea 10. The compressed air supply source 140 sucks air and compresses it, and then supplies the compressed air to the nozzle module 110.

For example, the compressed air supply source 140 may include an air compressor and a valve. The air compressor may be configured in a diaphragm type that sucks external air from an inlet through a filter and compresses it as a thin elastic plate reciprocates by a motor.

The valve may selectively supply the compressed air in the air compressor to the nozzle module 110 by opening and closing an outlet of the air compressor. The air compressor and valve may be controlled by the controller 130. The nozzle module 110 may be mounted on an outside of the compressed air supply source 140 to be connected to the compressed air supply source 140 in an air communication manner.

The infrared ray sensor 120 is disposed in the nozzle module 110 and emits infrared rays to the cornea 10 to measure an amount of light reflected from the cornea 10. Herein, the infrared rays refer to electromagnetic waves having a longer wavelength than visible rays.

The infrared ray sensor 120 is configured to emit infrared rays having a wavelength in a range that does not damage the cornea 10. The infrared ray sensor 120 may emit infrared rays to the cornea 10 to enable the system to measure intraocular pressure while preventing the subject from experiencing glare.

The infrared ray sensor 120 irradiates the entire surface of the cornea 10 with infrared rays and detects an amount of infrared rays reflected from the surface of the cornea 10. Therefore, even if the surface of the cornea 10 is irregular, it is possible to accurately measure the intraocular pressure.

The controller 130 converts the amount of light measured by the infrared ray sensor 120 before and after the deformation of the cornea 10 into intraocular pressure. When compressed air is applied to the cornea 10, the cornea 10 is deformed, and a curvature of the surface of the cornea 10 is changed according to a degree of the deformation of the cornea 10. A path of infrared rays reflected by the cornea 10 is changed due to a change in the curvature of the surface of the cornea 10 which is generated according to the intraocular pressure, such that a difference in the amount of infrared rays detected by the infrared ray sensor 120 occurs.

Accordingly, the controller 130 may determine whether or not glaucoma occurs by converting the amount of light measured by the infrared ray sensor 120 before and after the deformation of the cornea 10 into intraocular pressure using a correlation model indicating the correlation between the amount of infrared rays and the intraocular pressure.

The controller 130 may be mounted outside the compressed air supply source 140, or the controller 130 may be built into the compressed air supply source 140. The controller 130 may control the non-contact portable tonometry system 100 as a whole by receiving a system on/off command and an intraocular pressure measurement start command from a user through a user interface 131, and controlling the compressed air supply source 140 and the infrared ray sensor 120. The controller 130 may display the measured intraocular pressure through a display unit 136.

As described above, according to the non-contact portable tonometry system 100, the non-contact tonometry allows the subject to use it hygienically without any objection, and the infrared ray sensor 120 is integrated into the nozzle module 110 to make the system compact and portable. In addition, even if the surface of the cornea 10 is irregular, it is possible to accurately measure the intraocular pressure, and by applying a relatively inexpensive infrared ray sensor 120, the system can be easily developed for home use. As a result, even at home, patients can diagnose glaucoma in advance by themselves, enabling periodic eye examinations and early detection of glaucoma, and thereby minimizing damage due to the disease.

Meanwhile, the infrared ray sensor 120 may include a sensor support block 121, a light emitting element 122, and a pair of light receiving elements 123.

The sensor support block 121 is disposed in the nozzle module 110. The sensor support block 121 may include a block head 121a and a block body 121b. The block head 121a may be formed in a shape in which an outer diameter is gradually decreased toward a front end thereof facing the cornea 10. That is, the block head 121a may be formed in a shape tapered toward the front end thereof facing the cornea 10. The block head 121a may have a concavely curved groove in a form of a hemisphere or a dome from the front end.

The light emitting element 122 is disposed in the front groove of the block head 121a with a light emitting portion thereof being exposed to an outside, and the light receiving elements 123 are disposed therein with each light receiving portion thereof being exposed to the outside. In addition, when the system is further provided with pressure sensors 150, sensing portions of the pressure sensors 150 are disposed in the front groove of the block head 121a with sensing portions thereof being exposed to the outside. Accordingly, the front groove of the block head 121a may collect infrared rays reflected from the cornea 10 as much as possible to transmit them to the light receiving elements 123, and may collect the compressed air reflected by the cornea 10 as much as possible to transmit it to the pressure sensors 150.

The block body 121b may be coaxially connected to a rear end of the block head 121a in a cylindrical shape having an outer diameter smaller than the maximum outer diameter of the block head 121a. Accordingly, a boundary portion between the block body 121b and the block head 121a may be formed in a stepped shape. Therefore, the sensor support block 121 can be stably supported by the nozzle body 112 by placing the stepped portion around a fitting groove of the nozzle body 112 while the block body 121b is fitted in a fitting groove of the nozzle body 112. In addition, the stepped portion of the sensor support block 121 may be bonded around the fitting groove of the nozzle body 112 using an adhesive or the like.

The light emitting element 122 is supported by the sensor support block 121 to emit infrared rays to the cornea 10. The light emitting element 122 may include a light emitting diode that emits infrared rays. The light emitting element 122 may be controlled and driven by the controller 130.

The light emitting element 122 may be mounted by penetrating the sensor support block 121 in a longitudinal direction while the light emitting portion is exposed to the outside through a center of the front end groove of the block head 121a. The sensor support block 121 may expose the light emitting portion of the light emitting element 122 through an exposure hole having a smaller diameter than the hole through which the body of the light emitting element 122 is inserted.

The pair of light receiving elements 123 are respectively disposed on both sides of the light emitting element 122, and are supported by the sensor support block 121 to receive the light reflected from the cornea 10 and measure the amount of light. The light receiving element 123 may be formed of a photodiode or the like. The light receiving element 123 may convert the measured amount of light into an electrical signal and provide it to the controller 130.

That is, the light receiving elements 123 may measure the amount of light before and after the deformation of the cornea 10, convert the measured amount of light into an electrical signal, and provide it to the controller 130. The controller 130 may convert the electrical signal provided from the light receiving elements 123 before and after the deformation of the cornea 10 into intraocular pressure.

The light receiving elements 123 may be mounted in the sensor support block 121 by penetrating with being inclined closer to the center in the longitudinal direction while each receiving portion thereof is exposed to an outside through the center of the front end groove of the block head 121a. The light receiving elements 123 may be symmetrically disposed about the light emitting element 122. Accordingly, the light receiving elements 123 may receive the infrared rays reflected from the cornea 10 as much as possible.

To accurately measure the intraocular pressure, initial alignment of the nozzle module 110 with respect to the cornea 10 is important. When the nozzle module 110 is initially positioned with respect to the cornea 10, a difference in voltage measured by the pair of light receiving elements 123 may be used for initial alignment of the nozzle module 110 with respect to the cornea 10.

For example, when it is determined that the difference in the voltage measured by the light receiving elements 123 is within an allowable range, the controller 130 may recognize that the nozzle module 110 is positioned at a target position with respect to the cornea 10 and drive the compressed air supply source 140. When it is determined that the difference in the voltage measured by the light receiving elements 123 is out of the allowable range, the controller 130 may guide the subject to place the nozzle module 110 at the target position with respect to the cornea 10 by notifying through an alarm or the like.

Meanwhile, the nozzle module 110 may include a nozzle body 112 and a nozzle tip 113.

The nozzle body 112, in which the sensor support block 121 is fixed to the central portion thereof, has an air supply port 114 formed in an outer circumference portion thereof, through which the compressed air is supplied from the compressed air supply source 140. The nozzle body 112 may be formed in a shape having a body central part 112a, a first enlarged diameter part 112b, and a second enlarged diameter part 112c.

The body central part 112a has the fitting groove in the center into which the block body 121b of the sensor support block 121 is fitted from the front. The body central part 112a may be formed in a hollow cylinder shape whose front end is opened. The body central part 112a may have the stepped portion formed along the bottom edge thereof around the fitting groove, such that the rear end of the block body 121b may be seated and supported by the stepped portion. The body central part 112a may have holes formed in a lower surface of the fitting groove thereof, from which respective lead wires of the light emitting element 122, the light receiving elements 123, and the pressure sensors 150 are drawn out.

The first enlarged diameter part 112b is formed with an outer diameter larger than that of the body central part 112a along the outer circumference of the body central part 112a closer to the rear end side of the body central part 112a. The air supply port 114 may be formed by penetrating the outer circumference of the first enlarged diameter part 112b in the longitudinal direction. The air supply port 114 may be formed in a cut shape to a side surface of the first enlarged diameter part 112b. Two air supply ports 114 may be provided symmetrically arranged with respect to the first enlarged diameter part 112b. An air supply pipe 114a for connection with the compressed air supply source 140 may be mounted in the air supply port 114.

The first enlarged diameter part 112b forms an air flow passage between a front end portion of the body central part 112a and an inner circumference of the nozzle tip 113, such that the compressed air introduced from the air supply port 114 can be transferred to the air spray port 111 of the nozzle tip 113.

The second enlarged diameter part 112c is formed with an outer diameter larger than that of the first enlarged diameter part 112b along the outer circumference of the body central part 112a farther from the rear end of the body central part 112a than the first enlarged diameter part 112b. The second enlarged diameter part 112c has a stepped portion formed between the first enlarged diameter part 112b and the same, such that the rear end of the nozzle tip 113 may be seated and supported by the stepped portion. The stepped portion of the second enlarged diameter part 112c may be joined to the rear end of the nozzle tip 113 using an adhesive or the like.

The nozzle tip 113 has the air spray port 111 formed in the central portion to accommodate the sensor support block 121 together with the nozzle body 112. Compressed air supplied through the air supply port 114 is transmitted between the nozzle body 112 and the same, and sprayed through the air spray port 111. The nozzle tip 113 may be formed in a shape having a first tip part 113a and a second tip part 113b. The first tip part 113a may have a hollow cylinder shape whose front and rear ends are opened, and the rear end thereof may be supported in contact with the stepped portion of the second enlarged diameter part 112c. The second tip part 113b may be formed in a shape extending from the front end of the first tip part 113a having an outer diameter decreased toward the cornea 10. That is, the second tip part 113b may be formed in a shape tapered toward the front end facing the cornea 10. Since the second tip part 113b is formed to have the same taper angle as the taper angle of the block head 121a, a predetermined interval may be formed between an inner surface of the second tip part 113b and an outer surface of the block head 121a.

The second tip part 113b has the air spray port 111 formed at the front central portion thereof. The air spray port 111 may be formed in a circular shape. The air spray port 111 may have a diameter enough to expose the front end portion of the block head 121a. The compressed air introduced into the nozzle body 112 may flow evenly to the air spray port 111 along the flow passage between the first tip part 113a and the block head 121a, and then may be sprayed in a ring shape through the air spray port 111.

Meanwhile, the non-contact portable tonometry system may include the pressure sensors 150. The pressure sensors 150 are disposed in the nozzle module 110 to receive the compressed air which is sprayed from the nozzle module 110 and reflected by the cornea 10 to measure the pneumatic pressure.

When the compressed air is applied to the cornea 10, the cornea 10 is deformed, and a distance between the cornea 10 and the pressure sensor 150 is changed, such that a difference in the pneumatic pressure detected by the pressure sensor 150 occurs due to a difference in the distance therebetween. The controller 130 may convert the pneumatic pressure measured by the pressure sensor 150 before and after the deformation of the cornea 10 into intraocular pressure using a correlation model indicating the correlation between the pneumatic pressure and the intraocular pressure.

The system may be provided with the pair of pressure sensors 150. The pressure sensors 150 may be mounted in the sensor support block 121 by penetrating with being inclined toward the center based on the longitudinal direction while each sensing portion thereof is exposed to an outside through the center of the front end groove of the block head 121a between the light receiving elements 123. The pressure sensors 150 may be symmetrically disposed about the light emitting element 122. Accordingly, the pressure sensors 150 may receive the compressed air reflected by the cornea 10 as much as possible. Each of the pressure sensors 150 may be disposed at the same interval as that of the light receiving elements 123 arranged on both sides thereof.

Figure 7:
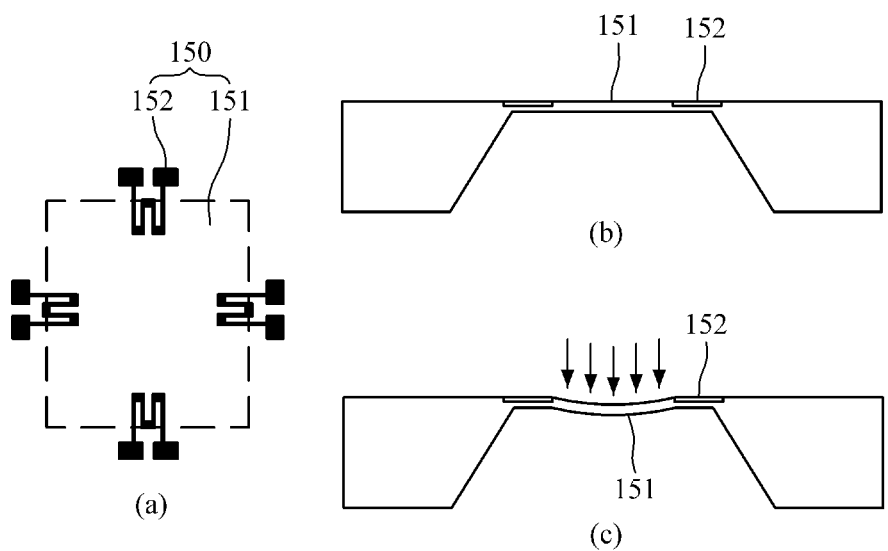
FIG. 7 is a schematic view illustrating an example of the configuration of a pressure sensor.

As an example, as shown in FIG. 7, the pressure sensor 150 may be configured as a piezoresistive pressure sensor including a diaphragm 151 and a piezoresistor 152. The diaphragm 151 is deformed by compressed air reflected by the cornea 10. The piezoresistor 152 may measure the pressure of compressed air by converting the amount of deformation of the diaphragm 151 into an electrical resistance value.

The pressure sensor 150 may convert the measured pneumatic pressure into an electrical signal to provide it to the controller 130. That is, the pressure sensor 150 may measure the amount of light before and after the deformation of the cornea 10, and convert it into an electrical signal, followed by providing to the controller 130. The controller 130 may convert the electrical signal provided from the pressure sensor 150 before and after the deformation of the cornea 10 into intraocular pressure.

The controller 130 may convert the pneumatic pressure measured by the pressure sensor 150 before and after the deformation of the cornea 10 into intraocular pressure in connection with the amount of light measured by the infrared ray sensor 120. For example, the controller 130 may enhance the ability to discriminate the intraocular pressure by supplementing the intraocular pressure value in various ways such as a method of calculating an average value by averaging values obtained by converting the pneumatic pressure measured by the pressure sensor 150 into the intraocular pressure and values obtained by converting the light amount measured by the infrared ray sensor 120 into the intraocular pressure, or selecting the maximum value among the obtained values before and after the deformation of the cornea 10.

A method for measuring intraocular pressure using a difference in infrared intensity according to an embodiment of the present invention will be described below.

First, compressed air is sprayed into the cornea of a subject through the air spray port to cause a corneal deformation.

Then, infrared rays are emitted to the cornea to measure an amount of light reflected from the cornea to the air spray port by the infrared ray sensor. In this case, the infrared rays are emitted to the cornea by the light emitting element, and the light reflected from the cornea is received by the light receiving elements disposed on both sides of the light emitting element to measure the amount of light.

Thereafter, the amount of light measured by the infrared ray sensor before and after the deformation of the cornea is converted into intraocular pressure by the controller. In a further embodiment, the compressed air reflected by the cornea may be received by the pressure sensor to measure the pneumatic pressure. In this case, the pneumatic pressure measured by the pressure sensor before and after the deformation of the cornea may be converted into intraocular pressure in connection with the amount of light measured by the infrared ray sensor.

Although the present invention has been described with reference to the embodiments shown in the drawings, these are merely an example. It should be understood by persons having common knowledge in the technical field to which the present invention pertains that various modifications of the embodiments may be made. Accordingly, the real technical protection scope of the present invention is determined by the technical spirit of the appended claims.

The invention claimed is:

1. A non-contact portable tonometry system for detecting an intraocular pressure, the system comprising:
    a nozzle assembly configured to receive compressed air from a compressed air supply source and spray the compressed air into a cornea of a subject through an air spray port to cause a corneal deformation and to generate reflected compressed air reflected from the cornea;
    a pressure sensor disposed in the nozzle assembly to receive the reflected compressed air to measure a pneumatic pressure;
    an infrared ray sensor disposed in the nozzle assembly to emit infrared rays to the cornea and measure an amount of light reflected from the cornea before and after the deformation of the cornea; and
    a controller configured to convert the pneumatic pressure measured by the pressure sensor after the deformation of the cornea in connection with the amount of the reflected light measured by the infrared ray sensor before and after the deformation of the cornea into the intraocular pressure,
    wherein the infrared ray sensor comprises:
    a sensor support block disposed in the nozzle assembly;
    a light emitting element supported by the sensor support block to emit the infrared rays to the cornea; and
    a pair of light receiving elements respectively disposed on both sides of the light emitting element and supported by the sensor support block to receive the light reflected from the cornea and measure the amount of light,
    wherein the sensor support block comprises a block head formed in a shape tapered toward a front end thereof, configured to face the cornea and having a concavely curved groove at the front end, and a block body connected to a rear end of the block head,
    wherein the light emitting element is mounted by penetrating the sensor support block in a longitudinal direction while a light emitting portion thereof is exposed to an outside through a center of the front end groove of the block head,
    wherein the light receiving elements are mounted in the sensor support block by penetrating with being inclined closer to a center in the longitudinal direction while each receiving portion thereof is exposed to an outside through the center of the front end groove of the block head,
    wherein the nozzle assembly comprises:
    a nozzle body in which the sensor support block is fixed at a central portion thereof and an air supply port for receiving the compressed air from the compressed air supply source is formed at an outer circumference portion; and
    a nozzle tip which has the air spray port formed in a central portion thereof to accommodate the sensor support block together with the nozzle body, and is configured to receive the compressed air supplied through the air supply port between the nozzle body and the nozzle tip to spray it through the air spray port, and
    wherein the nozzle tip comprises a first tip part having front and rear ends that are open, and a second tip part formed in a shape tapered toward a front end and configured to face the cornea, the second tip part having the air spray port formed at a front central portion thereof and configured to inject compressed air in a ring shape between the second tip part and the block head.

2. A tonometry method for detecting an intraocular pressure using the system according to claim 1, the method comprising:
    spraying compressed air into the cornea of the subject through the air spray port to cause the corneal deformation and to generate the reflected compressed air from the cornea;
    receiving the reflected compressed air to measure pneumatic pressure by the pressure sensor;
    emitting the infrared rays to the cornea to measure the amount of light reflected to the air spray port from the cornea by the infrared ray sensor; and
    converting the pneumatic pressure measured by the pressure sensor after the deformation of the cornea in connection with the amount of the reflected light measured by the infrared ray sensor before and after the deformation of the cornea into the intraocular pressure.

* * * * *